United States Patent
Yin et al.

(10) Patent No.: US 8,515,532 B2
(45) Date of Patent: Aug. 20, 2013

(54) COMPENSATION OF MOTION ARTIFACTS IN CAPACITIVE MEASUREMENT OF ELECTROPHYSIOLOGICAL SIGNALS

(75) Inventors: Bin Yin, Eindhoven (NL); Mohammed Meftah, Eindhoven (NL); Teunis Jan Ikkink, Geldrop (NL)

(73) Assignee: Koninklijke Philips N.V., Eindhoven (NL)

( * ) Notice: Subject to any disclaimer, the term of this patent is extended or adjusted under 35 U.S.C. 154(b) by 81 days.

(21) Appl. No.: 13/059,076

(22) PCT Filed: Aug. 24, 2009

(86) PCT No.: PCT/IB2009/053715
§ 371 (c)(1),
(2), (4) Date: Feb. 15, 2011

(87) PCT Pub. No.: WO2010/023615
PCT Pub. Date: Mar. 4, 2010

(65) Prior Publication Data
US 2011/0137200 A1    Jun. 9, 2011

(30) Foreign Application Priority Data
Aug. 29, 2008 (EP) .................................... 08163290

(51) Int. Cl.
*A61B 5/04* (2006.01)
*A61B 5/0408* (2006.01)
*A61B 5/05* (2006.01)
*A61B 5/053* (2006.01)

(52) U.S. Cl.
USPC ............ 600/546; 600/372; 600/547; 600/595

(58) Field of Classification Search
USPC .................................. 600/372, 547, 595, 546
See application file for complete search history.

(56) References Cited

U.S. PATENT DOCUMENTS

| | | | | |
|---|---|---|---|---|
| 4,213,467 A * | 7/1980 | Stulen et al. | .................. | 600/546 |
| 4,780,661 A * | 10/1988 | Bolomey et al. | .............. | 324/638 |
| 5,215,081 A * | 6/1993 | Ostroff | .............................. | 607/8 |
| 5,404,877 A * | 4/1995 | Nolan et al. | .................. | 600/484 |
| 6,434,421 B1* | 8/2002 | Taheri | .......................... | 600/547 |
| 6,438,413 B1* | 8/2002 | Taheri | .......................... | 600/547 |
| 6,807,438 B1 | 10/2004 | Del Re et al. | | |
| 2003/0032889 A1* | 2/2003 | Wells | ............................ | 600/546 |
| 2004/0073104 A1* | 4/2004 | Brun del Re et al. | ......... | 600/372 |
| 2004/0254435 A1 | 12/2004 | Mathews et al. | | |
| 2005/0113721 A1* | 5/2005 | Reed et al. | .................... | 600/595 |

(Continued)

FOREIGN PATENT DOCUMENTS

| | | |
|---|---|---|
| EP | 1674036 | 6/2006 |
| WO | WO2006031025 | 3/2006 |
| WO | WO2006066566 | 6/2006 |
| WO | WO2006111876 | 10/2006 |

*Primary Examiner* — Sean Dougherty

(57) ABSTRACT

The invention relates to a system and a method in which an electrophysiological signal is sensed capacitively with at least two closely spaced electrodes such that the electrodes experience strongly correlated skin-electrode distance variations. To be able to derive a motion artifact signal, the capacitive coupling between the electrodes and skin is made intentionally different. With a signal processing means the motion artifact signal can be removed from the measured signal to leave only the desired electrophysiological signal. Since the measured quantity is dependant on the electrode-skin distance itself, the system and method do not need to rely on the constancy of a transfer function. Hereby, they give reliable motion artifact free output signals.

13 Claims, 8 Drawing Sheets

(56) References Cited

U.S. PATENT DOCUMENTS

| | | | |
|---|---|---|---|
| 2005/0177038 A1* | 8/2005 | Kolpin et al. | 600/372 |
| 2006/0149341 A1* | 7/2006 | Palti | 607/63 |
| 2006/0173364 A1* | 8/2006 | Clancy et al. | 600/485 |
| 2006/0195020 A1* | 8/2006 | Martin et al. | 600/301 |
| 2006/0287608 A1* | 12/2006 | Dellacorna | 600/546 |
| 2007/0135701 A1* | 6/2007 | Fridman et al. | 600/382 |
| 2007/0179376 A1* | 8/2007 | Gerder | 600/393 |
| 2007/0208233 A1* | 9/2007 | Kovacs | 600/300 |
| 2008/0058656 A1* | 3/2008 | Costello et al. | 600/508 |
| 2008/0208063 A1* | 8/2008 | Brauers et al. | 600/481 |
| 2009/0018410 A1* | 1/2009 | Coene et al. | 600/301 |
| 2009/0030298 A1* | 1/2009 | Matthews et al. | 600/372 |

* cited by examiner

COMPENSATION OF MOTION ARTIFACTS IN CAPACITIVE MEASUREMENT OF ELECTROPHYSIOLOGICAL SIGNALS

FIELD OF THE INVENTION

The present invention relates to a system for providing motion compensated capacitive measurement of electrophysiological signals. Moreover, the invention is related to a signal processing unit, a method and computer program code for compensating for motion in the measurement of electrophysiological signal.

BACKGROUND OF THE INVENTION

Measurements of electrophysiological signals, such as the electric activity of the heart (ECG), the electrical activity produced by the muscles (EMG), and the electrical activity produced by the brain (EEG) of a human or animal body, are required in medical diagnoses and treatments, in clinical research and more and more in consumer healthcare products as well. Traditionally these signals are measured with electrodes that are connected to the skin via a galvanic contact, often using electrolytic glue. It is a disadvantage of this kind of measurement that it may cause skin irritation during prolonged usage, it may restrict the patient or user from free moving and it typically provides less comfort for the patient or user.

In order to overcome the above disadvantages, contactless measurement of the electrophysiological signals may be used. An example of such a contactless measurement is a capacitive measurement, wherein a capacitor is effectively formed in which the human or animal tissue acts as one of the capacitor plates and an electrode plate of a sensor probe acts as the other capacitor plate. In the capacitive sensing, no galvanic contact to the skin is needed, whereby the need for preparation of the skin of the human or animal body and a sticky patch with conductive gel for establishing a good electrical contact is alleviated. This is in particular advantageous, when a longitudinal measurement has to be conducted.

It is a problem of the capacitive electrophysiological sensors the measurement signal may be influenced significantly by the movements of a user whose electrophysiological signals are to be measured. Such influence of the measurement signal is denoted motion-induced artifact, and it is due to the fact that the coupling capacitance is changing due to skin-electrode distance variation induced by movements of the user, causing deterioration of the measured electrophysiological signal.

The above problem is described in U.S. Pat. No. 6,807,438 and WO2006066566.

U.S. Pat. No. 6,807,438 makes use of the fact that effective capacitance is inversely proportional to the skin-electrode distance and that the variation of capacitance with distance is less sensitive at larger distances. U.S. Pat. No. 6,807,438 discloses reducing motion artifacts by intentionally increasing the gap between the electrode plate and the skin. A disadvantage of this solution is that also the sensitivity of the sensor to the probed electrical potential decreases, i.e. the signal amplitude is sacrificed, due to decreased signal-to-noise ratio, for a reduction of motion artifacts. The motion artifacts may be reduced, but they are not eliminated.

In WO2006066566 a method is described in which an electrical signal of known frequency is injected into the human body. By determining the amplitude variation of the corresponding signal as picked up by the capacitive plate, an estimate can be made of the variation of the distance of the two capacitor plates. In this way a variation in the skin-electrode distance can be detected and possibly its impact on measured signals can be compensated for. A disadvantage of this method is that safety issues might play a role related to the injection of currents into the body.

Another investigated approach for motion artifact reduction is the use of motion-sensing technologies, e.g. accelerometers, to measure the amount of motion at the ECG electrode site and to use adaptive filtering techniques to reduce or even remove the motion artifact from the electrophysiological signal. A disadvantage of this approach is that the transfer function from measured quantity, viz. the acceleration, towards electrode-skin distance can be allowed to vary only slowly with time compared to both the electrophysiological signal and the electrode-skin distance itself. This transfer function is dependent on the mechanical configuration of the sensor to skin attachment. The transfer function of an elastic attachment may be constant over time, if no other parts can mechanically interfere. However, if for example clothing is worn over the sensor, it may exert pressure on the sensor, which changes the transfer function accordingly in an unpredictable way. These transfer function changes are induced by movements of the person and therefore typically occur at similar time scales as the changes of electrode-skin distance. Hence the adaptation time constant in an adaptive filtering approach would ideally have to be in the same order as that of the movement, making it prone to instability and/or lack of precision.

Hence, an improved system for compensation for motion artifacts in capacitive measurement of electrophysiological signals would be advantageous, and in particular a more efficient and/or reliable system would be advantageous.

SUMMARY OF THE INVENTION

Accordingly, the invention preferably seeks to mitigate, alleviate or eliminate one or more of the above mentioned disadvantages singly or in any combination. In particular, it may be seen as an object of the present invention to provide a system for providing capacitive measurement of electrophysiological signals that solves the above mentioned problems of the prior art with regard to motion induced artifacts.

This object and several other objects are obtained in a first aspect of the invention by providing a system for providing motion compensated capacitive measurement of electrophysiological signals, the system comprising:

a sensor probe comprising a first and a second capacitive plate arranged to be placed in the proximity of the skin of a human or animal body, wherein the first capacitance between the first capacitive plate and the skin of the human or animal body is different from the second capacitance between the second capacitive plate and the skin of the human or animal body, and wherein the first and second capacitive plates are arranged for providing a first and second measurement signal as a measure of an electrophysiological signal of the human or animal body, processor means arranged for:
  receiving first and second measurement signals from the first and second capacitive plates;
  determining a motion modulated signal from the first and/or second measurement signals;
  providing a motion compensated output signal from the motion modulated signal and the first and/or second measurement signals.

The invention is particularly, but not exclusively, advantageous for obtaining a reliable motion compensated capacitive measurement of an electrophysiological signal of a user's body. By arranging two or more capacitive plates within the sensor probe for sensing one and the same electrophysiological signal from the human or animal body, a reliable and precise elimination of motion artifacts is achievable.

The first and second capacitive plates are arranged in close proximity to each other in order to provide closely related measurements of the same electrophysiological signal and/or strongly correlated skin-electrode distance variations. The first and second capacitive plates may for instance be concentric and/or be placed with a small distance between them. Hereby, when the probe is placed adjacent to a human or animal body, the first and second capacitive plates may be regarded as being placed at substantially the same position of the body.

The term "human or animal body" is meant to denote the body of a user of a patient. For shortness' sake, the term "user" is used in the following to denote a "human or animal body". The probe of the system is arranged for being placed in proximity to the skin of such a user, where the term "proximity" is meant to denote that the probe is placed at such a distance from the skin of the user that a useable measurement of the electrophysiological signal is obtainable. Practical examples of the sensor probe being in the proximity to the user is when the sensor probe is placed adjacent to or at a small distance from the skin, e.g. at a distance of the order of millimeters, such as e.g. 0 to 15 mm, preferably at 0 to 10 mm. Moreover, the term "capacitive plate" is meant to be synonymous to the term "capacitor plate" and thus to mean one of the plates or conductors of a capacitor. In the sensor probe of the invention, each of the two or more capacitive plates is arranged for establishing a capacitive coupling to the skin of a user, so that a capacitor is formed in which the human or animal tissue acts as one of the capacitor plates and the capacitive plate of the sensor acts as the other capacitor plate. In the system of the invention, two or more capacitors are formed by the two or more capacitive plates and the tissue of the user.

In another aspect, the sensor probe moreover comprises an active shield in order to eliminate electromagnetic interference.

In an embodiment of the system according to the invention, the first and second capacitive plates have different distances to a measurement surface of the sensor probe and/or the first and second capacitive plates have mutually different areas. Hereby it is ensured that the first and second capacitances are different from each other, which enables a reliable determination of the motion induced artifacts in output signals from the first and second capacitive plates. The term "measurement surface" of the sensor probe is meant to denote the surface thereof arranged to be placed facing the skin of a user.

In another embodiment of the system, the motion modulated signal is determined by calculating the difference of the first measurement signal and a factor applied to the second measurement signal. This motion modulated signal effectively corresponds to a factor multiplied by the change in distance between the skin and the sensor probe multiplied by the input signal, where the factor depends on the first and second capacitance, a first distance between the first capacitive plate and the skin and a second distance between the second capacitive plate and the skin. However, estimating the motion modulated signal does not need to directly estimate the distance change and the input signal. Instead, the estimation may be done indirectly as shown in equation (8) below.

In yet another embodiment of the system, the determination of the motion modulated signal comprises averaging or low pass filtering of the first and second measurement signals over a predetermined time interval. Hereby, a drift of the nominal distance between the skin of a user and the sensor may be taken into account in the determination of the motion compensated output signal. The nominal distance between the skin and the sensor is the distance in the case of no motion, and a "drift" of the distance is meant to denote any slow variations thereof.

In yet another embodiment, the provision of the motion compensated output signal comprises using a least-mean-square algorithm to adaptively remove the effect of the motion modulated signal from the first and/or second measurement signals.

In a second aspect, the invention relates to a signal processing unit for compensating for motion, said signal processing unit comprising means for receiving first and second measurement signals from a sensor probe comprising a first and a second capacitive plate arranged to be placed in the proximity of the skin of a human or animal body, wherein the first capacitance between the first capacitive plate and the skin of the human or animal body is different from the second capacitance between the second capacitive plate and the skin of the human or animal body, wherein the first and second measurement signals are measures of an electrophysiological signal of the human or animal body, wherein said signal processing unit is arranged for determining a motion modulated signal from the first and/or second measurement signals; and providing a motion compensated output signal from the motion modulated signal and the first and/or second measurement signals.

In a third aspect, the invention relates to a method for providing motion compensated capacitive measurement of electrophysiological signals, the method comprising:

placing a sensor probe in the proximity of the skin of a human or animal body, wherein said sensor probe comprises a first and a second capacitive plate, wherein the first capacitance between the first capacitive plate and the skin of the human or animal body is different from the second capacitance between the second capacitive plate and the skin of the human or animal body, providing a first and second measurement signals as a measure of an electrophysiological signal from the first and second capacitive plates;

determining a motion modulated signal from the first and/or second measurement signals; and providing a motion compensated output signal from the motion modulated signal and the first and/or second measurement signals.

In a fourth aspect, the invention relates to a sensor probe for providing motion compensated capacitive measurement of electrophysiological signals, the probe comprising a first and a second capacitive plate arranged to be placed in the proximity of the skin of a human or animal body, wherein the first capacitance between the first capacitive plate and the skin of the human or animal body is different from the second capacitance between the second capacitive plate and the skin of the human or animal body, and wherein the first and second capacitive plates are arranged for providing a first and second measurement signal as a measure of an electrophysiological signal of the human or animal body.

In a fifth aspect, the invention relates to a computer program product being adapted to enable a computer system comprising at least one computer having data storage means associated therewith to control a signal processing unit according to the third aspect of the invention.

This aspect of the invention is particularly, but not exclusively, advantageous in that the present invention may be implemented by a computer program product enabling a computer system to perform the operations of the third aspect of the invention. Thus, it is contemplated that some known signal processing unit may be changed to operate according to the present invention by installing a computer program product on a computer system controlling the system. Such a computer program product may be provided on any kind of computer readable medium, e.g. magnetically or optically based medium, or through a computer based network, e.g. the Internet.

The first, second, third, fourth and fifth aspect of the present invention may each be combined with any of the other aspects. These and other aspects of the invention will be apparent from and elucidated with reference to the embodiments described hereinafter.

BRIEF DESCRIPTION OF THE FIGURES

The present invention will now be explained, by way of example only, with reference to the accompanying Figures, where.

DETAILED DESCRIPTION OF AN EMBODIMENT

Figure 1:
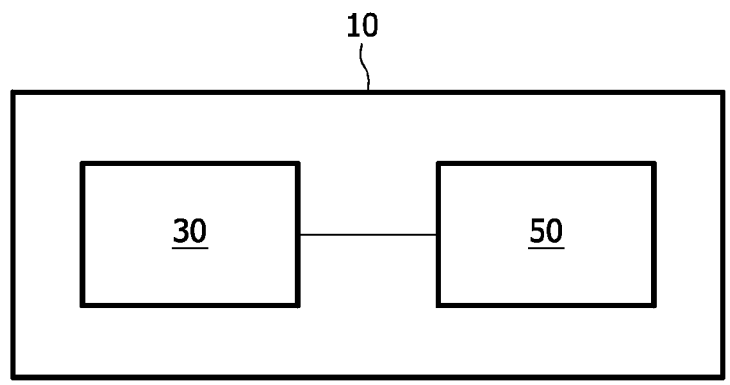
FIG. 1 is a schematic block diagram of an embodiment of the system of the invention.

FIG. 1 is a schematic block diagram of an embodiment of the system 10 of the invention. The system 10 comprises a sensor probe 30 as well as processor means 50 arranged for communicating with the sensor probe 30. The processor means 50 may be connected to the sensor probe 30 in any appropriate way, wired or wirelessly, as long as measurement signals from the probe 30 may be communicated to the processor means 50.

Figure 2:
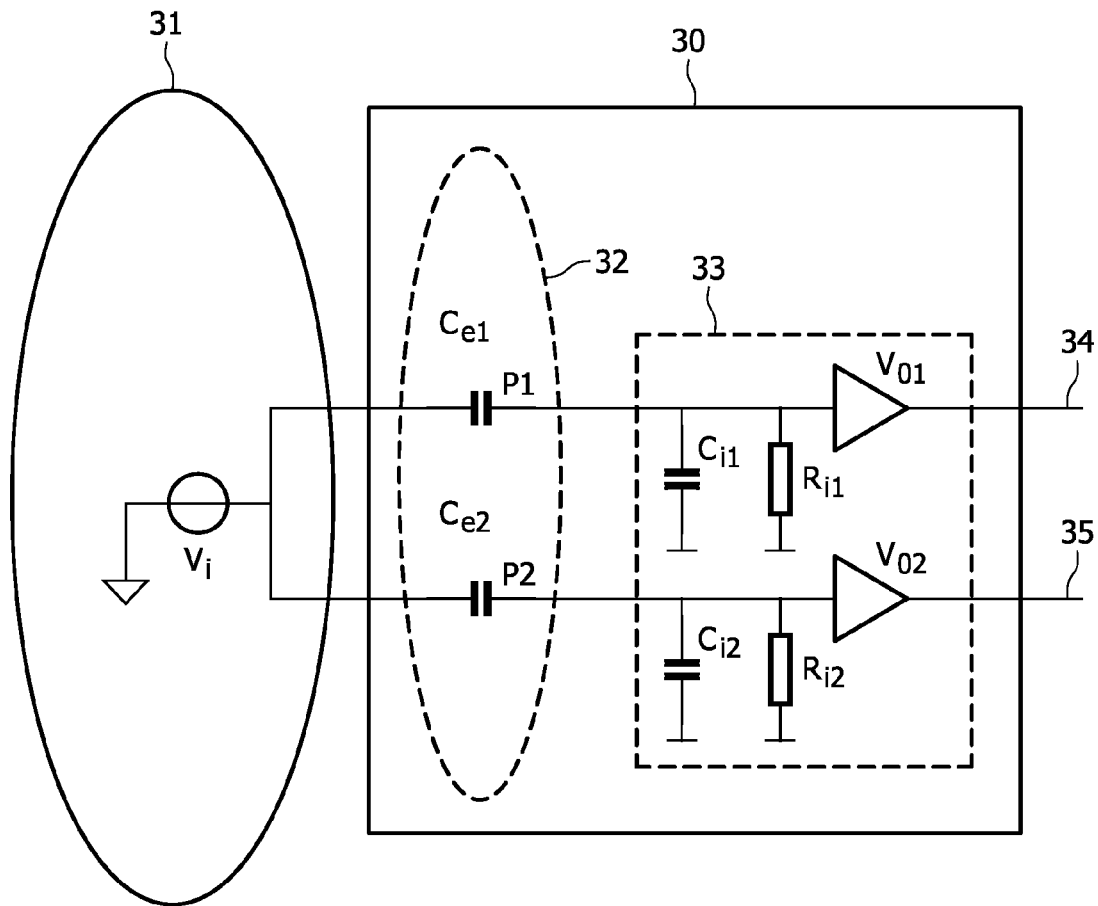
FIG. 2 is a schematic drawing of an embodiment of the sensor probe of the invention.

FIG. 2 is a schematic drawing of an embodiment of the sensor probe 30 of the invention. In the following, a sensor probe 30 having two electrodes operating as capacitive plates is discussed. It is stressed, that such a dual capacitive sensor is discussed only as an example, and that more than two electrodes may be used in one sensing probe.

FIG. 2 shows the sensor probe 30 arranged in the vicinity of tissue of a human or animal body 31, said tissue having a potential $V_t$. The sensor probe 30 may be seen as comprising a measurement part or a sensor part 32 and an amplification part 33. The sensor part of the sensor probe comprises two capacitive sensor plates P1, P2 arranged in two capacitive measurement channels. Even though the symbol of a capacitor is shown in FIG. 2, it is stressed that the probe 30 for each capacitive channel only comprises one sensor plate P1 or P2, which in use is placed in the proximity of the skin of a user so that the tissue of the user will act as the other capacitor plate. The sensor illustrated in the drawings has two plates P1 and P2, which in use provide two capacitive couplings with the tissue of a user so as to provide capacitive measurement at almost the same position of the probe in relation to the user tissue. The first capacitance $C_{e1}$ between the first capacitive plate P1 and the skin of the human or animal body is made different from the second capacitance $C_{e2}$ between the second capacitive plate P2 and the skin of the human or animal body. The first and second capacitive plates P1, P2 are arranged for providing a first and second measurement signal $V_{O1}$, $V_{O2}$ at outputs 34, 35 as a measure of an electrophysiological signal of the human or animal body, after amplification in the amplification circuit 33, where $C_{i1}$, $R_{i1}$ are the input capacitance and resistance of the first channel amplifier, and $C_{i2}$, $R_{i2}$ are the input capacitance and resistance of the second channel amplifier. The two coupling capacitor plates P1 and P2 of the probe are placed so close that they effectively measure the same signal of the user.

Figure 3:
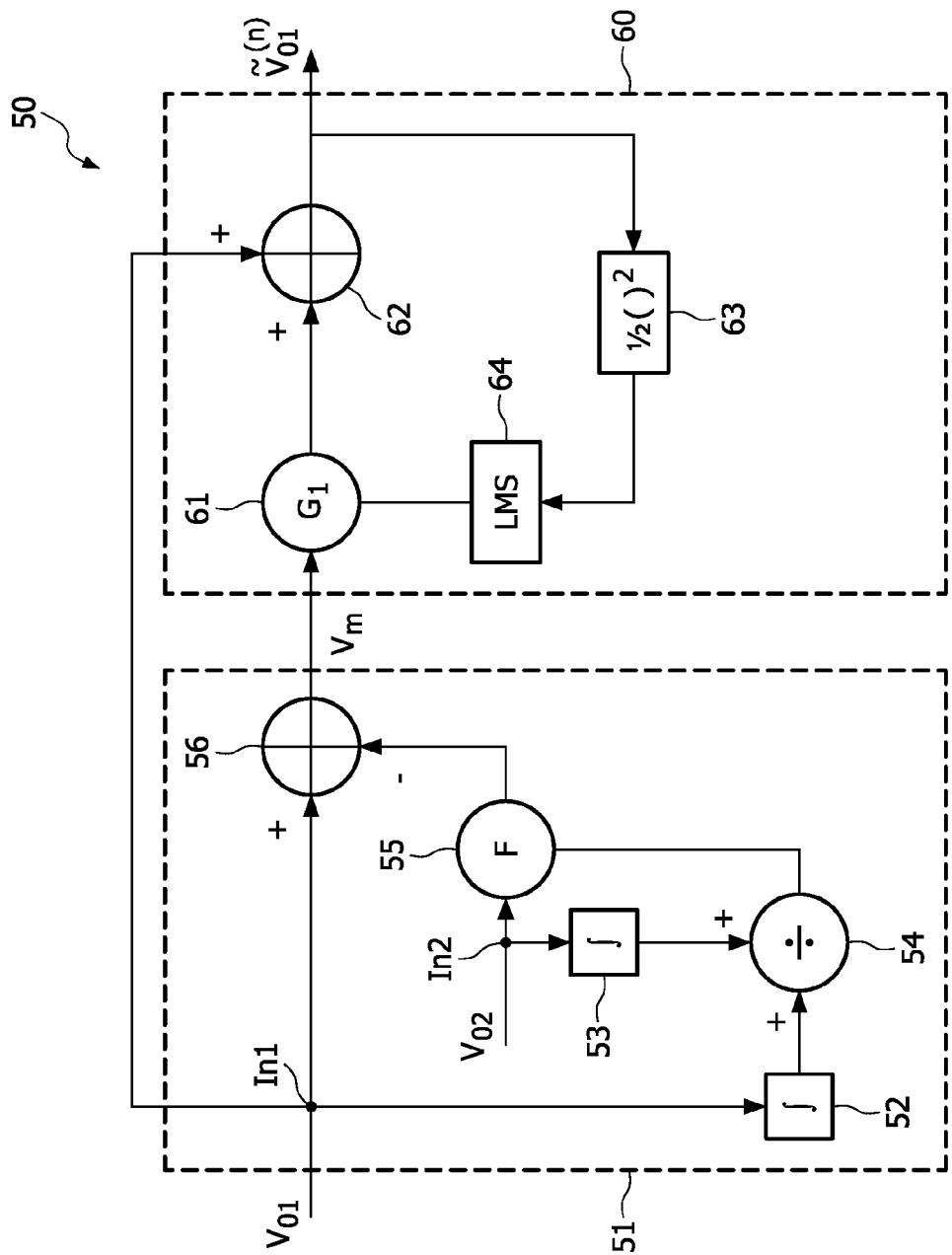
FIG. 3 is a block diagram of circuit diagram equivalent to an embodiment of the processor means of the invention.

FIG. 3 is a block diagram of circuit diagram 50 equivalent to an embodiment of the processor means of the invention. The circuit diagram 50 may be seen so as to comprise a motion detection part 51 and a motion compensation part 60. The first measurement signal $V_{O1}$ from the first capacitive channel of the sensor probe (not shown in FIG. 3) is received at input In1 and is input to an integrator block 52. The second measurement signal $V_{O2}$ from the second capacitive channel of the sensor probe is received at input In2 and is input to an integrator block 53. In the division block 54 the ratio F between the integrated measurement signals $V_{O1}$, $V_{O2}$ is found. The signal $V_m$ is a motion modulated signal derived from $V_{O1}$, $V_{O2}$ by calculating the difference of a factor F applied to the signal $V_{O2}$ subtracted from the first measurement signal $V_{O1}$ in block 56. The motion modulated signal $V_m$ corresponds to the motion artifact signal being the effect of motion of the probe on the measurement signals $V_{O1}$, $V_{O2}$. The first measurement signal $V_{O1}$ is compensated for motion by use of the motion modulated signal $V_m$ in the motion compensation part 60 of the circuit diagram 50. A function $G_1$ in block 61 is learned by minimizing a target function J in a least mean square (LMS) algorithm in block 64. The motion compensated output signal $\hat{V}_{O1}^{(n)}$ is achieved by adding the factor $G_1$ multiplied by the motion modulated signal $V_m$ to the first measurement signal $V_{O1}$ in block 62.

FIGS. 4a-4c, 5a-5c and 6a-6c show different embodiments of a sensor probe according to the invention. The sensor probe may incorporate processor means (not shown) in order to provide motion artifact free or motion compensated output signals. Alternatively, the output from the shown probes may be the first and second measurement signals $V_{O1}$, $V_{O2}$ for subsequent processing in order to remove motion artifacts.

In the three embodiments shown, an electrophysiological signal is sensed with two closely spaced electrodes that experience strongly correlated skin-electrode distance variations. To be able to derive a motion artifact signal the coupling capacitances are made different on purpose. The following embodiments illustrate how the coupling capacitances can be made different. As mentioned earlier, the invention is not limited to capacitive measurement channels with two coupling capacitors, i.e. using more than two electrodes in a single sensing probe is thus possible.

Figure 4A:
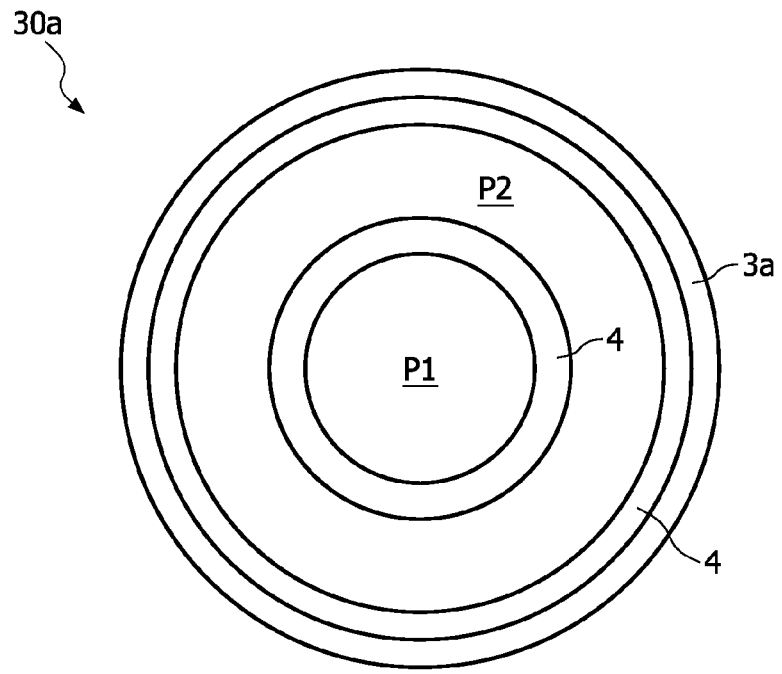
FIGS. 4a, 4b and 4c are views of the front side, a cross section an the back side of a probe 30a according to the invention.
Figure 4B:
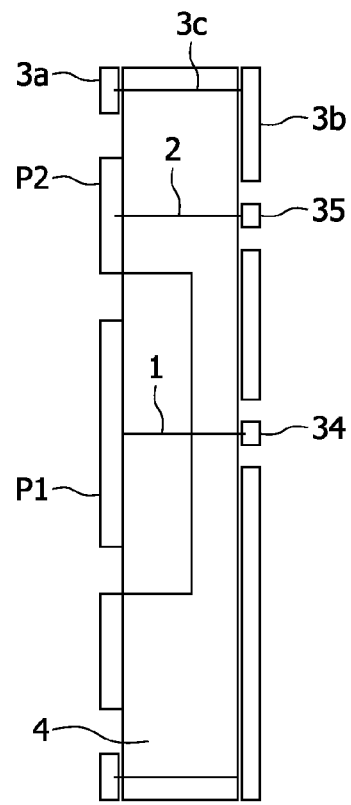
Figure 4C:
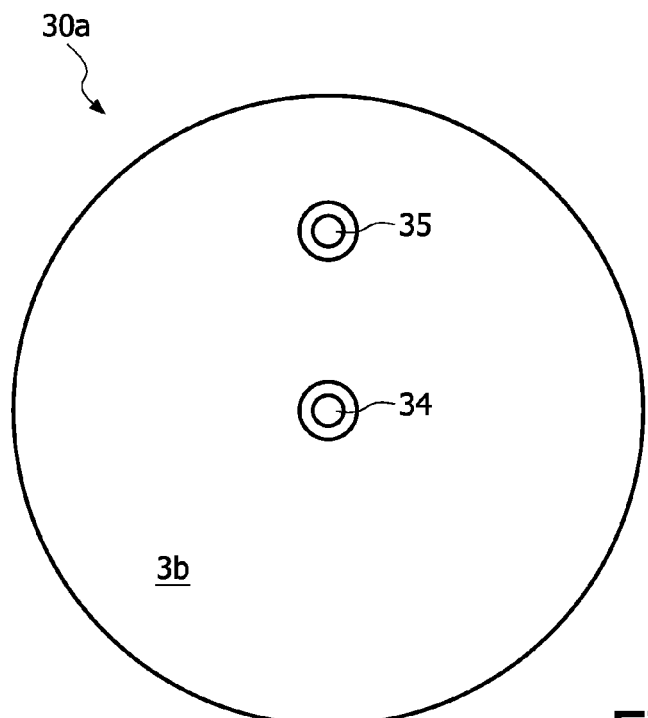

FIGS. 4a, 4b and 4c are views of the front side, a cross section and the back side of a probe 30a according to the invention. The sensor probe 30a comprises a first capacitive plate P1 and a second capacitive plate P2 arranged on an electrode carrier 4 of an electrically insulating material, such as the material of PCB, e.g. Kapton. The sensor probe 30a moreover comprises an active shield 3a, 3b, 3c which is arranged for guarding the sensor plates P1, P2 from electromagnetic interferences.

From FIG. 4b it may be seen that the first capacitive plate P1 arranged at the front side of the sensor probe (viz. the side arranged to be placed against the skin of a user) is electrically connected to an output 34 at the back side of the sensor probe (viz. the side arranged to be directed away from the skin of a user) via a electrical connection 1. Likewise, the second capacitive plate P2 arranged at the front side of the sensor probe is electrically connected to an output 35 at the back side of the sensor probe via an electrical connection 2, and a front side portion 3a of the shield is connected to a back side portion 3b thereof via an electrical connection 3c.

In the embodiment of FIGS. 4a-4c, the capacitive coupling between the first capacitive plate P1 and a user is made different from the capacitive coupling between the second capacitive plate P2 and the user by making the areas of the first and second capacitive plates P1, P2 different. The first and second capacitive plates P1, P2 are concentric circular plates ensuring that they are placed at substantially the same position of the body in order to measure the same electrophysiological signal.

Figure 5A:
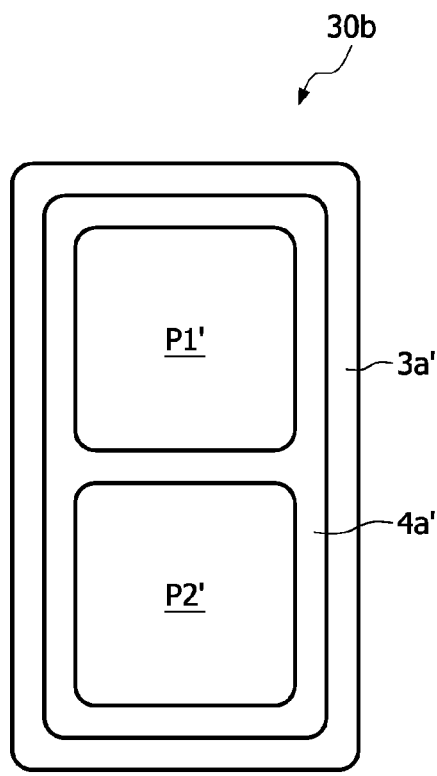
FIGS. 5a, 5b and 5c are views of the front side, a cross section an the back side of an alternative probe 30b according to the invention.
Figure 5B:
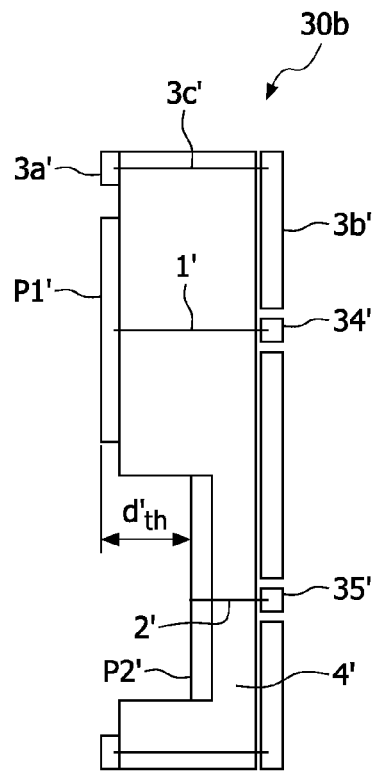
Figure 5C:
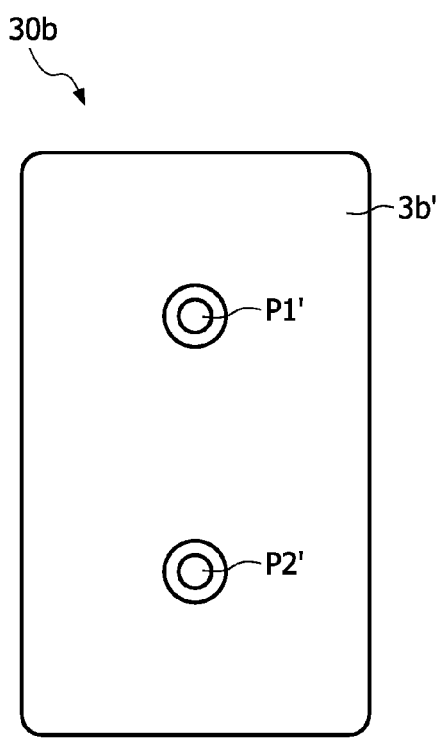

FIGS. 5a, 5b and 5c are views of the front side, a cross section and the back side of an alternative probe 30b according to the invention. The sensor probe 30b comprises a first capacitive plate P1' and a second capacitive plate P2' arranged on an electrode carrier 4' of an electrically insulating material, such as the material of PCB, e.g. Kapton. The sensor probe 30b moreover comprises an active shield 3a', 3b', 3c' which is arranged for guarding the sensor plates P1', P2' from electromagnetic interferences.

From FIG. 5b it may be seen that the first capacitive plate P1' arranged at the front side of the sensor probe is electrically connected to an output 34' at the back side of the sensor probe via an electrical connection 1'. Likewise, the second capacitive plate P2' arranged at the front side of the sensor probe is electrically connected to an output 35' at the back side of the sensor probe via a electrical connection 2', and a front side portion 3a' of the shield is connected to a back side portion 3b' thereof via an electrical connection 3c'.

In the embodiment of FIGS. 5a-5c, the distance between the first electrode P1' and the front side of the sensor probe 30b is made different from the distance between the second electrode P2' and the front side of the sensor probe 30b. The difference in distance is denoted $d'_{th}$. This difference $d'_{th}$ ensures a difference in the capacitive coupling between the first capacitive plate P1' and a user compared to the capacitive coupling between the second capacitive plate P2' and the user when the areas of the first and second capacitive plates P1', P2' are identical. Of course, other different electrode geometries are conceivable in order to achieve different skin-electrode distances, viz. distances between the electrodes and the front side of the sensor probe.

Figure 6A:
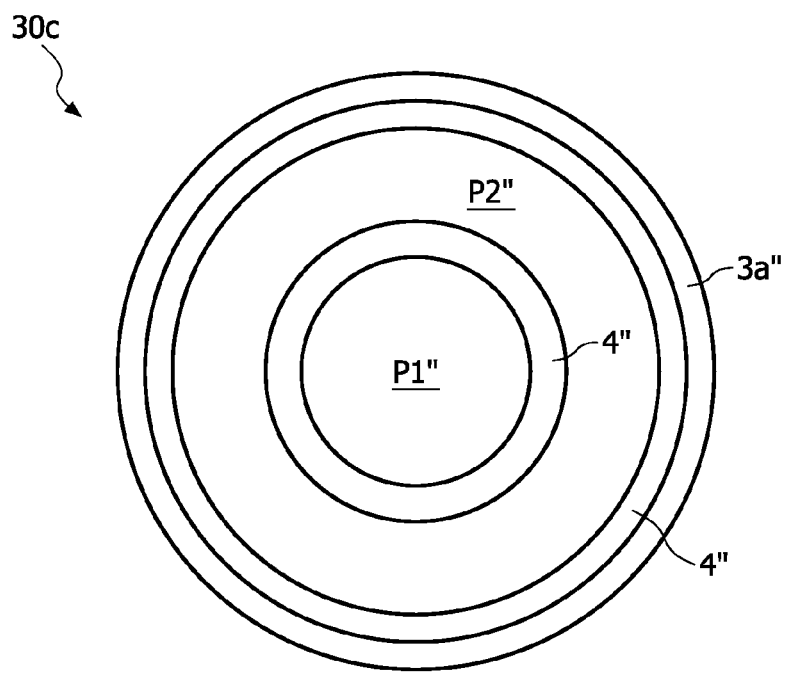
FIGS. 6a, 6b and 6c are views of the front side, a cross section an the back side of another alternative probe 30c according to the invention.
Figure 6B:
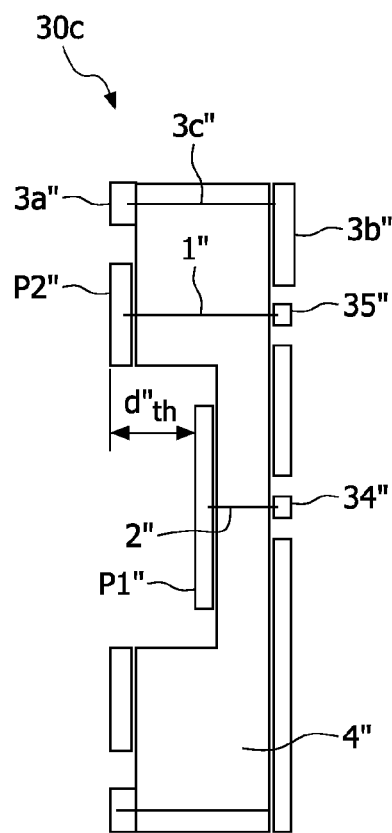
Figure 6C:
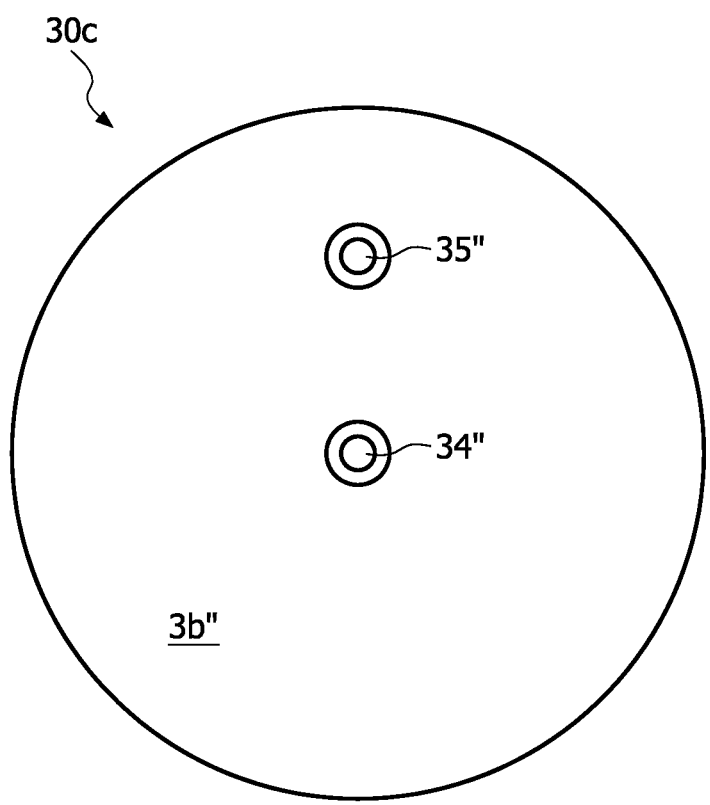

FIGS. 6a, 6b and 6c are views of the front side, a cross section and the back side of yet another probe 30c according to the invention. This embodiment may be seen as a combination of the embodiments in FIGS. 4a-4c and 5a-5c in that a dual channel sensor probe is proposed with both different electrode areas and different skin-electrode distances.

The sensor probe 30c comprises a first capacitive plate P1" and a second capacitive plate P2" arranged on an electrode carrier 4" of an electrically insulating material, such as PCB. The sensor probe 30c moreover comprises an active shield 3a", 3b", 3c" which is arranged for guarding the sensor plates P1", P2" from electromagnetic interferences.

From FIG. 6b it may be seen that the first capacitive plate P1" arranged at the front side of the sensor probe is electrically connected to an output 34" at the back side of the sensor probe via an electrical connection 1". Likewise, the second capacitive plate P2" arranged at the front side of the sensor probe is electrically connected to an output 35" at the back side of the sensor probe via a electrical connection 2", and a front side portion 3a" of the shield is connected to a back side portion 3b" thereof via an electrical connection 3c".

In the embodiment of FIGS. 6a-6c, the distance between the first electrode P1" and the front side of the sensor probe 30c is different from the distance between the second electrode P2" and the front side of the sensor probe 30c. The difference in distance is denoted $d''_{th}$. Moreover, the areas of the first and second capacitive plates P1", P2" are made different. These two differences in distance and area ensure a difference in the capacitive coupling between the first capacitive plate P1" and a user compared to the capacitive coupling between the second capacitive plate P2" and the user. Of course, other different electrode geometries are conceivable in order to achieve different skin-electrode distances.

Figure 7:
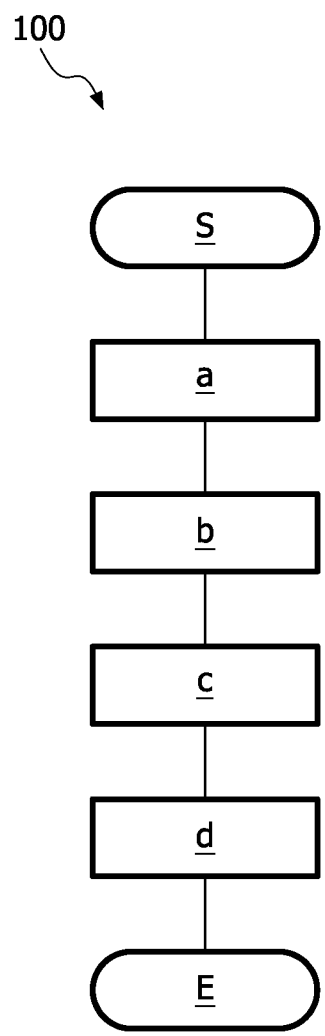
FIG. 7 is a flow-chart of a method according to the invention.

FIG. 7 is a flow-chart of a method 100 according to the invention, for providing motion compensated capacitive measurement of electrophysiological signals. The method 100 starts at S and comprises the step (a) of placing a sensor probe in the proximity of the skin of a human or animal body. The sensor probe may be a sensor probe as shown in FIGS. 4a-4c, 5a-5c or 6a-6c. The sensor probe comprises a first and a second capacitive plate wherein, where the first capacitance between the first capacitive plate and the skin of a user is different from the second capacitance between the second capacitive plate and the skin of the user.

In the subsequent step (b) a first and second measurement signals are provided as a measure of an electrophysiological signal from the first and second capacitive plates.

Subsequently, in step (c) a motion modulated signal is determined from the first and/or second measurement signals, and in the subsequent step (d) a motion compensated output signal ($\hat{V}_{o1}^{(n)}$) is provided from the motion modulated signal and the first and/or second measurement signals. The method ends in E.

An example of the processing in order to perform the steps of the method 100 is described in the following with reference to the FIGS. 2 and 3.

With reference to FIG. 2, the transfer functions of the two channels, namely from $V_{o1}$ to $V_i$ and from $V_{o2}$ to $V_i$, are given by $$H_1(j\omega) = \frac{C_{e1}}{C_{e1} + C_{i1}} \cdot \frac{j\omega R_{i1}(C_{e1} + C_{i1})}{j\omega R_{i1}(C_{e1} + C_{i1}) + 1}, \quad (1)$$

$$H_2(j\omega) = \frac{C_{e2}}{C_{e2} + C_{i2}} \cdot \frac{j\omega R_{i2}(C_{e2} + C_{i2})}{j\omega R_{i2}(C_{e2} + C_{i2}) + 1},$$

respectively. Note that, for a differential measurement that is usually adopted for the purpose of getting rid of the common mode signal (e.g., the 50 Hz signal coming from an AC power supply), two circuits of this type are required.

On the basis of the measured signals $V_{o1}$ and $V_{o2}$, a motion-modulated signal $V_m$ may be derived and subsequently used in removing the motion-induced disturbance in $V_{o1}$ (or $V_{o2}$) to get $\hat{V}_{o1}^{(n)}$ (or $\hat{V}_{o2}^{(n)}$) that is free of motion-artifacts.

It is assumed that in a nominal situation, viz. a situation with no motion artifacts, the two sensing channels have effective coupling capacitances:

$$C_{e1} = \varepsilon_1 \frac{A_1}{d_1} \text{ and } C_{e2} = \varepsilon_2 \frac{A_2}{d_2}, \quad (2)$$

Where $\varepsilon_1$, $\varepsilon_2$ are permitivities, $A_1$, $A_2$ are the areas of the first and second capacitor plates P1, P2 and $d_1$, $d_2$ are the distances between the first and second capacitor plates P1, P2 and the skin of a user, when the sensor probe is in use.

The capacitances $C_{e1}$ and $C_{e2}$ are made different by, for instance, taking an electrode in the first channel having an area 2 times as big as that of the electrode in the second channel, i.e., $A_1 = 2A_2$. From (1), the steady-state readouts for the two channels are given by $$V_{o1}^{(n)} = \frac{C_{e1}}{C_{e1} + C_{i1}} V_i, \quad V_{o2}^{(n)} = \frac{C_{e2}}{C_{e2} + C_{i2}} V_i. \quad (3)$$

In a practical measurement, because the capacitor plates are so closely spaced, the skin-plate-distance variations they experience induced by a motion are strongly correlated. In a simplified case, this can be described as $$\Delta d_1 = \Delta d \text{ and } \Delta d_2 = k\Delta d, \quad (4)$$

where k represents a factor that may be negative. The readouts become $$V_{o1} = \frac{C_{e1}}{C_{e1} + C_{i1} + C_{i1} \frac{\Delta d}{d_1}} V_i, \quad V_{o2} = \frac{C_{e2}}{C_{e2} + C_{i2} + C_{i2} \frac{\Delta d}{d_2}} V_i. \quad (5)$$

Using Taylor series expansion in the skin-plate-distance change $\Delta d$ and omitting the high order terms, provides:

$$V_{o1} \approx V_{o1}^{(n)} - V_{m1}, \quad (6)$$
$$V_{o2} \approx V_{o2}^{(n)} - V_{m2},$$
where $$V_{o1}^{(n)} = \frac{C_{e1}}{C_{e1} + C_{i1}} V_i, \quad V_{m1} = \frac{C_{e1} C_{i1}}{(C_{e1} + C_{i1})^2} \frac{\Delta d}{d_1} V_i, \quad (7)$$
$$V_{o2}^{(n)} = \frac{C_{e2}}{C_{e2} + C_{i2}} V_i, \quad V_{m2} = \frac{C_{e2} C_{i2}}{(C_{e2} + C_{i2})^2} \frac{k\Delta d}{d_2} V_i.$$

The omitting of the high orders is rationalized by the facts that $$\frac{C_{i1}}{C_{e1} + C_{i1}} < 1 \text{ and } \frac{C_{i2}}{C_{e2} + C_{i2}} < 1, \text{ and } \frac{\Delta d}{d_1} < 1, \frac{k\Delta d}{d_2} < 1$$

when $d_1$, and $d_2$, are designed to be sufficiently big. (6) implies that a measurement result in the presence of motion artifacts can be approximated with two components, one free of motion artifacts and the other one that is modulated by the skin-plate-distance change $\Delta d$.

In the motion detection part of the proposed scheme, a motion signal can be, based on (6), derived as $$V_m = V_{o1} - F \cdot V_{o2} = M \cdot \Delta d V_i \quad (8)$$
where $$F = \frac{C_{e1}}{C_{e1} + C_{i1}} \frac{C_{e2} + C_{i2}}{C_{e2}}, \text{ and} \quad (9)$$

$$M = \left( \frac{C_{i2}}{C_{e2} + C_{i2}} \frac{k}{d_2} - \frac{C_{i1}}{C_{e1} + C_{i1}} \frac{1}{d_1} \right) \frac{C_{e1}}{C_{e1} + C_{i1}}.$$

The signal $V_m$ is the input signal $V_i$ modulated by the skin-plate-distance variation $\Delta d$, up to a factor M. Making use of the motion signal $V_m$, a least-mean-square (LMS) algorithm is able to adaptively remove the motion-induced signal component $V_{m1}$ (or $V_{m2}$) from $V_{o1}$ (or $V_{o2}$).

Taking $V_{o1}$ as an example, in the motion compensation part, the cleaned signal can be obtained by $$\tilde{V}_{o1}^{(n)} = V_{o1} + G_1 V_m \quad (10)$$

where $G_1$ is learned by minimizing the target function $$J(G_1) = E\left\{ \frac{1}{2} [\tilde{V}_{o1}^{(n)}]^2 \right\}. \quad (11)$$

E{ } represents the mathematical expectation. The update rule for $G_1$ is given by $$G_1^{(k+1)} = G_1^{(k)} + \mu_1 \left( -\frac{\partial J(G_1)}{\partial G_1} \right), \quad (12)$$

where $\mu_1$ is a positive factor controlling the update rate. The update in (12) will reach an equilibrium state when $\partial J(G_1)/\partial G_1$, on average, approaches zero, leading to $$G_1 = \frac{(C_{e2} + C_{i2}) C_{i1} d_2}{(C_{e1} + C_{i1}) C_{i2} k d_1 - (C_{e2} + C_{i2}) C_{i1} d_2}. \quad (13)$$

Substituting (13) into (10) and using (6) and (7), one can readily get $$\tilde{V}_{o1}^{(n)} = V_{o1}^{(n)}.$$

Thus, the scheme illustrated in FIGS. 2 and 3 provides a signal measuring means that is insensitive to motions.

The nominal skin-to-plate distances $d_1$ and $d_2$ may drift during measurement, causing variations of $C_{e1}$ and $C_{e2}$ and in turn variation of the factor F over time. The variation of F is expected to be slow compared to that of $\Delta d$. It may be, as depicted in FIG. 3, updated by following the ratio between the magnitudes of $V_{o1}$ and $V_{o2}$ which can be obtained, for instance, by means of averaging or low pass filtering of $V_{o1}$ and $V_{o2}$ over a certain time interval. F needs update also because $C_{i1}$ and $C_{i2}$ can be slowly time varying.

Apparently, M would be also time varying not only due to slow drifting of coupling capacitances but also due to possibly fast changing of k. Therefore, the update rate $\mu_1$ of $G_1$ should be properly tuned to be able to follow that.

To be more general, the mutual association between the skin-to-plate distance changes experienced by the electrodes can be described by a filter K, instead of a scalar k. Accordingly, M becomes a filter as well, and a filter $G_1$ needs to be learned.

In general, the invention relates to a system and a method in which an electrophysiological signal is sensed capacitively with at least two closely spaced electrodes such that the electrodes experience strongly correlated skin-electrode distance variations. To be able to derive a motion artifact signal, the capacitive coupling between the electrodes and skin is made intentionally different. With a signal processing means the motion artifact signal can be removed from the measured signal to leave only the desired electrophysiological signal.

Since the measured quantity is dependant on the electrode-skin distance itself, the system and method do not need to rely on the constancy of a transfer function. Hereby, they give reliable motion artifact free output signals.

This invention may be relevant for any medical and healthcare devices, CE products and other applications where electrophysiological signal (e.g., ECG, EMG, EEG and etc.) measurements, especially by means of contactless (capacitive coupling), are performed.

The invention can be implemented in any suitable form including hardware, software, firmware or any combination of these. The invention or some features of the invention can be implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The invention claimed is:

1. A system for providing motion compensated capacitive measurement of electrophysiological signals, the system comprising:
a sensor probe comprising a first capacitive plate and a second capacitive plate arranged to be placed in a proximity of a skin of a human or animal body, wherein a first capacitance between the first capacitive plate and the skin is different from a second capacitance between the second capacitive plate and the skin, and wherein the first capacitive plate is connected to an input of a first amplifier for providing a first measurement signal and the second capacitive plate is connected to an input of a second amplifier for providing a second measurement signal as a measure of an electrophysiological signal of the human or animal body; and
a processor connected to the sensor probe and configured for performing the acts of:
receiving said first and second measurement signals from the first and second capacitive plates;
determining a motion modulated signal from at least one signal of the first measurement signal and the second measurement signal; and
providing a motion compensated output signal from the motion modulated signal and the at least one signal.

2. The system according to claim 1, wherein the first and second capacitive plates of the sensor probe have mutually different areas.

3. The system according to claim 1, wherein the sensor probe moreover comprises an active shield.

4. The system according to claim 1, wherein the determining act comprises calculating a difference between the first measurement signal and a factor applied to the second measurement signal, and wherein the factor is a ratio between the first and second measurement signals integrated by respective integrators.

5. The system according to claim 1, wherein the determination act comprises averaging or low pass filtering of the first and second measurement signals over a predetermined time interval.

6. The system according to claim 1, wherein the providing act comprises using a least-mean-square algorithm to adaptively remove the effect of the motion modulated signal from the at least one signal.

7. The system according to claim 1, wherein the first and second capacitive plates are placed so close that they effectively measure the same signal of the user.

8. The system according to claim 1, wherein the first and second capacitive plates of the sensor probe have different distances to a measurement surface of the sensor probe.

9. The system according to claim 1, wherein the first and second capacitive plates of the sensor probe have different distances to a measurement surface of the sensor probe and the first and second capacitive plates have mutually different areas.

10. A signal processing unit for compensating for motion, said signal processing unit comprising:
a first amplifier configured to receive a first measurement signal from a first capacitive plate of a sensor probe arranged to be placed in a proximity of a skin of a human or animal body; and
a second amplifier configured to receive a second measurement signal from a second capacitive plate of the sensor probe, wherein a first capacitance between the first capacitive plate and the skin is different from a second capacitance between the second capacitive plate and the skin, wherein the first and second measurement signals are measures of an electrophysiological signal of the human or animal body, said signal processing unit being configured for performing the acts of:
determining a motion modulated signal from the first and/or second measurement signals; and
providing a motion compensated output signal at least one signal of the first measurement signal and the second measurement signal.

11. A non-transitory computer readable medium embodying computer instructions executable by a processor to enable a computer system comprising at least one computer having a data storage associated therewith to control a signal processing unit according to claim 10.

12. A method for providing motion compensated capacitive measurement of electrophysiological signals, the method comprising the acts of:
placing a sensor probe in a proximity of a skin of a human or animal body, wherein said sensor probe comprises a first capacitive plate and a second capacitive plate, wherein a first capacitance between the first capacitive plate and the skin is different from a second capacitance between the second capacitive plate and the skin;
providing a first measurement signal from the first capacitive plate to an input of a first amplifier;

providing a second measurement signal from the second capacitive plate to an input of a second amplifier, the first and second measurement signals being a measure of an electrophysiological signal from the first and second capacitive plates;

determining a motion modulated signal from at least one signal of the first measurement signal and the second measurement signal; and providing a motion compensated output signal from the motion modulated signal and the at least one signal.

13. A sensor probe for providing motion compensated capacitive measurement of electrophysiological signals, the probe comprising:

a first capacitive plate connectable to an input of a first amplifier;

a second capacitive plate connectable to an input of a second amplifier, wherein the first capacitive plate and the second capacitive plate are arranged to be placed in a proximity of the a of a human or animal body, wherein a first capacitance between the first capacitive plate and the skin is different from the second capacitance between the second capacitive plate and the skin, and wherein the first and second capacitive plates are arranged for providing a first measurement signal and a second measurement signal as a measure of an electrophysiological signal of the human or animal body.

* * * * *